United States Patent [19]
Ling et al.

[11] Patent Number: 5,771,914
[45] Date of Patent: Jun. 30, 1998

[54] FLEXIBLE FLUID JUNCTION

[75] Inventors: Michael T. K. Ling, Vernon Hills; Lecon Woo, Libertyville, both of Ill.; Eric J. Hénaut, Arquennes; Patrick Balteau, Ohey, both of Belgium; Eric P. Loh, Park Ridge, Ill.; Francesco Peluso, Heverlee; Alphonse Heremans, Genappe, both of Belgium; Ying-Cheng Lo, Green Oaks, Ill.; Marc Bellotti, Libertyville, Ill.; Rafael A. Castellanos, Roselle, Ill.; Robin Peters, McHenry, Ill.

[73] Assignee: Baxter International Inc., Deerfield, Ill.

[21] Appl. No.: 799,855

[22] Filed: Feb. 13, 1997

[51] Int. Cl.⁶ ........................................ E03B 1/00
[52] U.S. Cl. .......................... 137/1; 137/597; 137/605; 251/9; 604/27; 604/283; 604/284
[58] Field of Search ............................. 251/4, 9; 137/597, 137/605, 1; 604/27, 30, 32, 34, 256, 28, 250, 283, 284

[56] References Cited

U.S. PATENT DOCUMENTS

| | | |
|---|---|---|
| 526,338 | 9/1894 | Alexander ........................... 251/9 |
| 3,724,461 | 4/1973 | Eisenberg ........................... 251/4 |
| 3,734,154 | 5/1973 | Polk .................................. 251/4 |
| 4,047,844 | 9/1977 | Robinson ........................... 251/9 |
| 4,676,476 | 6/1987 | Herrli ................................ 251/9 |
| 4,736,925 | 4/1988 | Kamstrup-Larsen ............... 251/4 |
| 4,942,886 | 7/1990 | Timmons ........................... 251/9 |
| 4,944,485 | 7/1990 | Daoud ............................... 251/9 |
| 4,951,665 | 8/1990 | Schneider ........................ 604/284 |
| 5,277,224 | 1/1994 | Hutton ............................. 137/597 |
| 5,348,592 | 9/1994 | Ellis ................................ 604/284 |

Primary Examiner—Denise L. Ferensic
Assistant Examiner—Ramyar Farid
Attorney, Agent, or Firm—Charles R. Mattenson; Thomas S. Borecki; Robert M. Barrett

[57] ABSTRACT

A flexible fluid junction that links three or more fluid ducts is provided. The junction includes a pair of flexible webs with at least three tubes or fluid ducts disposed between the flexible webs. The outer periphery of the webs is sealed together and around the tubes to define a chamber. An end of each tube terminates inside the chamber so that fluid may flow from each tube through the chamber. Still further, a method of manufacturing a flexible fluid junction and a method of using a flexible fluid junction are also provided.

15 Claims, 3 Drawing Sheets

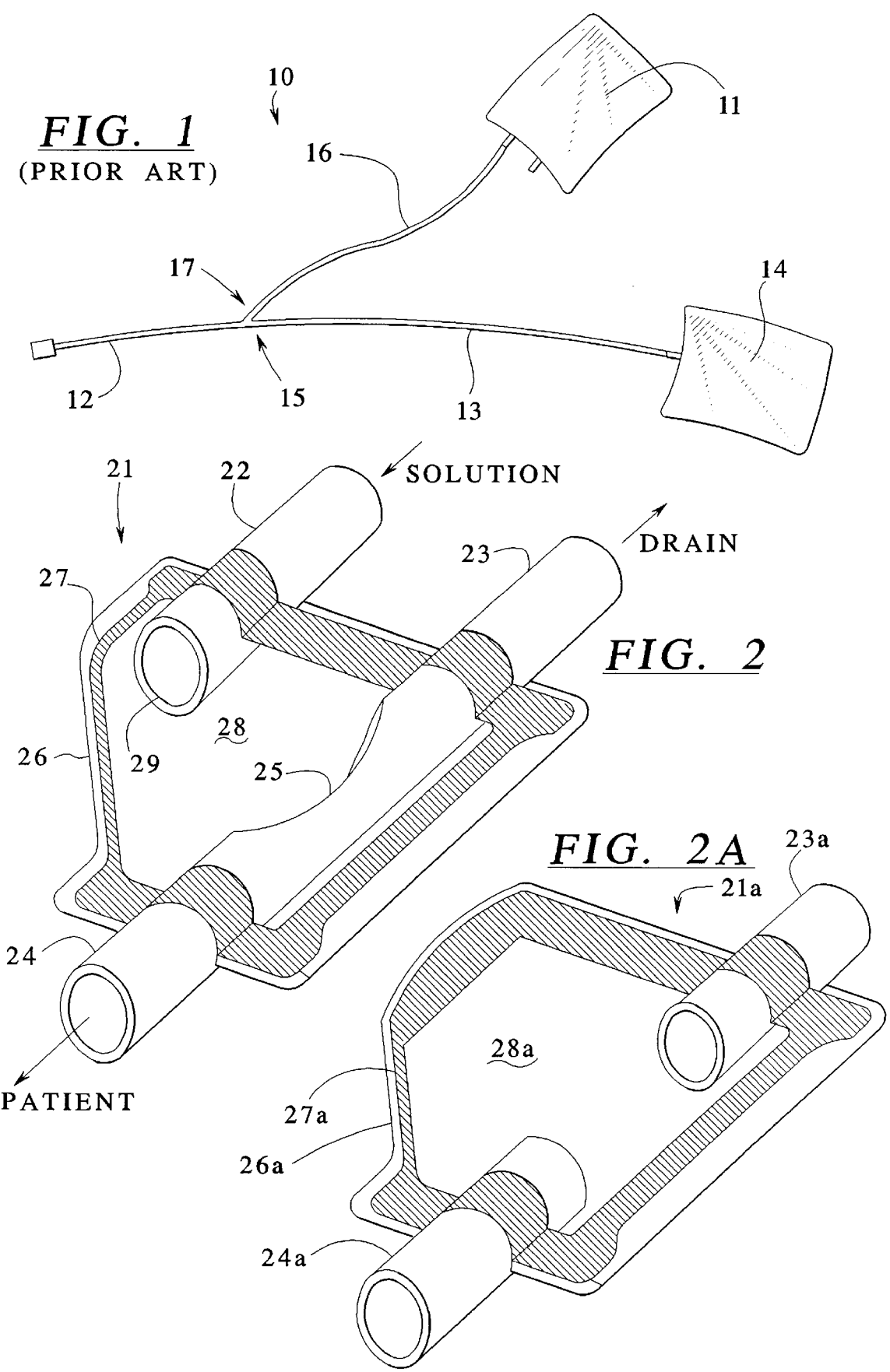

FLEXIBLE FLUID JUNCTION

BACKGROUND OF THE INVENTION

The present invention relates generally to apparatuses for connecting three or more fluid ducts or tubes. More specifically, the present invention relates to apparatuses for connecting three or more fluid ducts that also provide a flexible chamber disposed between the ducts.

In many medical procedures, there is a need to link two or more containers with the patient. One such example is peritoneal dialysis where at least one filled solution container is linked with the peritoneal cavity of the patient which, in turn, is also linked with a drainage container. The solution container, peritoneal cavity and drainage container must be linked by a three-way junction. However, a simple Y-shaped junction formed from plastic tubing is often not satisfactory because there is no efficient way to completely isolate one duct from the other two ducts. Specifically, if a simple Y-shaped junction is utilized, the duct to be isolated must be clamped at least a few inches away from the junction in order to avoid applying an excessive amount of stress to the junction, thereby risking breakage or cracking of the junction or requiring excessive force by patient to clamp. Clamping away from the junction allows the opportunity to collect contamination or air bubbles in the isolated leg.

Isolation of one or more tubes at a junction is important. Specifically, in the case of peritoneal dialysis, it is important to remove air bubbles from the solution tube before communication between the solution tube and the patient connector is established. Specifically, referring to FIG. 1, a system 10 for delivering dialysis solution from a solution container bag 11 to a patient by way of a patient connector 12 is illustrated. Typically, a connection is first made between the patient and the patient connector 12. Then flow is established through the patient line 12, through the drain line 13 and into the drain bag 14. When the drainage is complete, the patient line 12 is clamped off. Then, the clamp 15 is removed and solution is flushed through the line 16 to remove any air bubbles. In order to establish communication between the bag of fresh solution 11 and the patient connector 12, a clamp must be placed at the Y-shaped junction shown generally at 15 in order to isolate the solution line 16 from the drain line 13. An appropriate place for the clamp is indicated generally at the arrow 17.

However, as illustrated in FIG. 1, it is difficult to clamp the Y-shaped junction close to the point where the solution line 16 meets the patient line 12 and drain line 13. If a mechanical clamp is employed, clamping the solution line 16 close to the Y-shaped junction 15 is difficult or can result in damage to the junction 15. The same is true if it is desired to isolate the drain line 13 from the patient connector 12 and the solution line 16 or if it is desired to isolate the patient connector 12 from the solution line 16 and drain line 13.

Further, the Y-shaped junction illustrated in FIG. 1 is normally manufactured by an injection molding process. This process is relatively costly when compared to less expensive processes such as extrusion processes. Because the injection molded Y-shaped junction illustrated in FIG. 1 is a relatively rigid structure, it would be very difficult to expand the junction 15 to accommodate four tubes or lines, such as two container lines, a drain line and a patient connector. In any event, if such a modification were made, the injection-molded junction would be very hard to clamp and therefore very hard to isolate one or more lines from the other lines.

Therefore, a need exists for an improved fluid junction capable of connecting three or more fluid tubes. Such a junction should be flexible and easy to clamp so that the user can isolate one or more fluid ducts from the other fluid ducts. Further, such a junction should be preferably made from an extrusion process as opposed to an injection-molded process.

SUMMARY OF THE INVENTION

The present invention provides an improved flexible fluid junction capable of joining three or more fluid ducts, tubes or lines. The flexible fluid junction of the present invention includes a pair of flexible webs and at least two tubes disposed between the two flexible webs. The outer peripheries of the webs are sealed together around the tubes to define a chamber. An end of each tube terminates inside the chamber. The chamber, which is defined by the inside surfaces of the two webs and the sealed outer peripheries of the two webs, provides a flexible mixing chamber for the fluid which can be easily clamped to isolate any one or more tubes from the remaining tubes.

In an embodiment, two of the tubes are connected together with an aperture disposed between the two tubes and within the chamber.

In an embodiment, the flexible fluid junction includes three tubes. The three tubes may include one pair of tubes joined together with an aperture disposed therebetween, the aperture being disposed within the chamber.

In an embodiment, the flexible fluid junction includes four tubes. The four tubes may also comprise two pairs of tubes joined together with an aperture disposed therebetween, the apertures being disposed within the chamber.

In a preferred embodiment, the webs are formed by an extrusion process.

In an embodiment, the flexible fluid junction may also include a clamp that extends across the exterior surfaces of the webs. The clamp, when in a closed position, presses the interior surfaces of the webs together and isolates one or more tubes from the remaining tubes.

In an embodiment, the clamp may include an upper and lower arm that are pivotally connected together. One of the arms may include a latch for engaging a distal end of the other arm to hold the clamp in a closed position.

In an embodiment, the webs comprise a film consisting of polyvinylchloride (PVC).

In an embodiment, the webs comprise a film consisting of PVC coated, laminated or coextruded with a copolyester such as the copolyesters sold under the tradename PCCE by Eastman Chemical Company.

In an embodiment, the webs comprise a film consisting of a polyester block copolymer such as the polyester block copolymers sold under the tradename HYTREL by DuPont or a copolyester polymer containing a lubricant such as that sold under the tradename ACRAWAX by Lonza, Inc.

In an embodiment, the web comprises a film consisting of HYTREL containing ACRAWAX.

In an embodiment, the webs comprise a multilayer material which may include, for example, an upper layer which has high temperature strength and high temperature die release, a middle layer which is a mixture of ethylene vinyl acetate and an ionomer and a lower layer which is a mixture of polypropylene and a thermoplastic elastomer.

In a preferred embodiment, the outer peripheries of the webs are sealed together by radio frequencies or RF.

In an embodiment, the present invention provides a method of manufacturing a flexible fluid junction comprising the steps of providing a pair of flexible webs and at least three tubes, inserting one end of each of the tubes between the flexible webs and thereafter sealing the outer peripheries of the webs together around the tubes to define a chamber.

In an embodiment, the present invention provides an improved fluid exchange system that can be used for peritoneal dialysis. A solution container, a drainage container and a patient connector are all connected using a flexible fluid junction of the present invention.

In an embodiment, the present invention provides a method of linking at least two containers, including a solution container and a drainage container, to at least one supply tube without introducing air bubbles to the patient tube. The method includes the steps of providing at least two containers, including one solution container and one drainage container, providing a flexible fluid junction as described above with one tube being designated as the patient tube, one tube being designated as the drain tube and one tube being designated as the solution tube. The solution tube is first isolated from the drain and patient tubes with a clamp. After the drain tube is connected to the drain container and the patient tube is connected to the source of waste fluid, e.g. the peritoneal cavity of a patient, the solution container is connected to the solution tube. While the solution tube is isolated from the drain and patient lines, fluid flow is established between the source of waste fluid and the drain container to drain waste fluid and to remove any contamination from the connection. Then, the patient line is closed, the clamp is removed and solution may proceed from the solution tube into the drainage container. Both tubes are free of air bubbles and therefore no air is transmitted to the peritoneal cavity of the patient. Then, the clamp is moved to the drain line and the patient line is opened. The fresh dialysate flows into the patient.

An advantage of the present invention is that it provides an improved flexible fluid junction capable of connecting three or more fluid ducts.

Another advantage of the present invention is that it provides an improved flexible fluid junction that is easily clamped thereby enabling the user to isolate one or more fluid ducts from the remaining fluid ducts.

Yet another advantage of the present invention is that it provides an improved flexible fluid junction that is manufactured using extrusion processes as opposed to injection molding processes.

Still further, an advantage of the present invention is that it provides a flexible fluid junction that enables the manufacturer to control flow rates through the junction by adjusting the thickness of the film used to make the webs.

Another advantage of the present invention is that it provides a flexible fluid junction that enables the manufacturer to control flow rates through the junction by adjusting the size of the mixing chamber.

Moreover, an advantage of the present invention is that it provides a flexible fluid junction that can be clamped to close or shut off the patient of solution once the fluid exchange has been completed.

Additional features and advantages of the present invention are described in, and will be apparent from, the detailed description of the presently preferred embodiments and from the drawings.

BRIEF DESCRIPTION OF THE DRAWINGS

FIG. 1 illustrates the use of a prior art Y-shaped junction for linking three fluid ducts.

FIG. 2 illustrates a flexible fluid junction made in accordance with the present invention that links three fluid ducts.

FIG. 2A illustrates a flexible fluid junction made in accordance with the present invention that links two fluid ducts.

DETAILED DESCRIPTION OF THE PRESENTLY PREFERRED EMBODIMENTS

Figure 5:
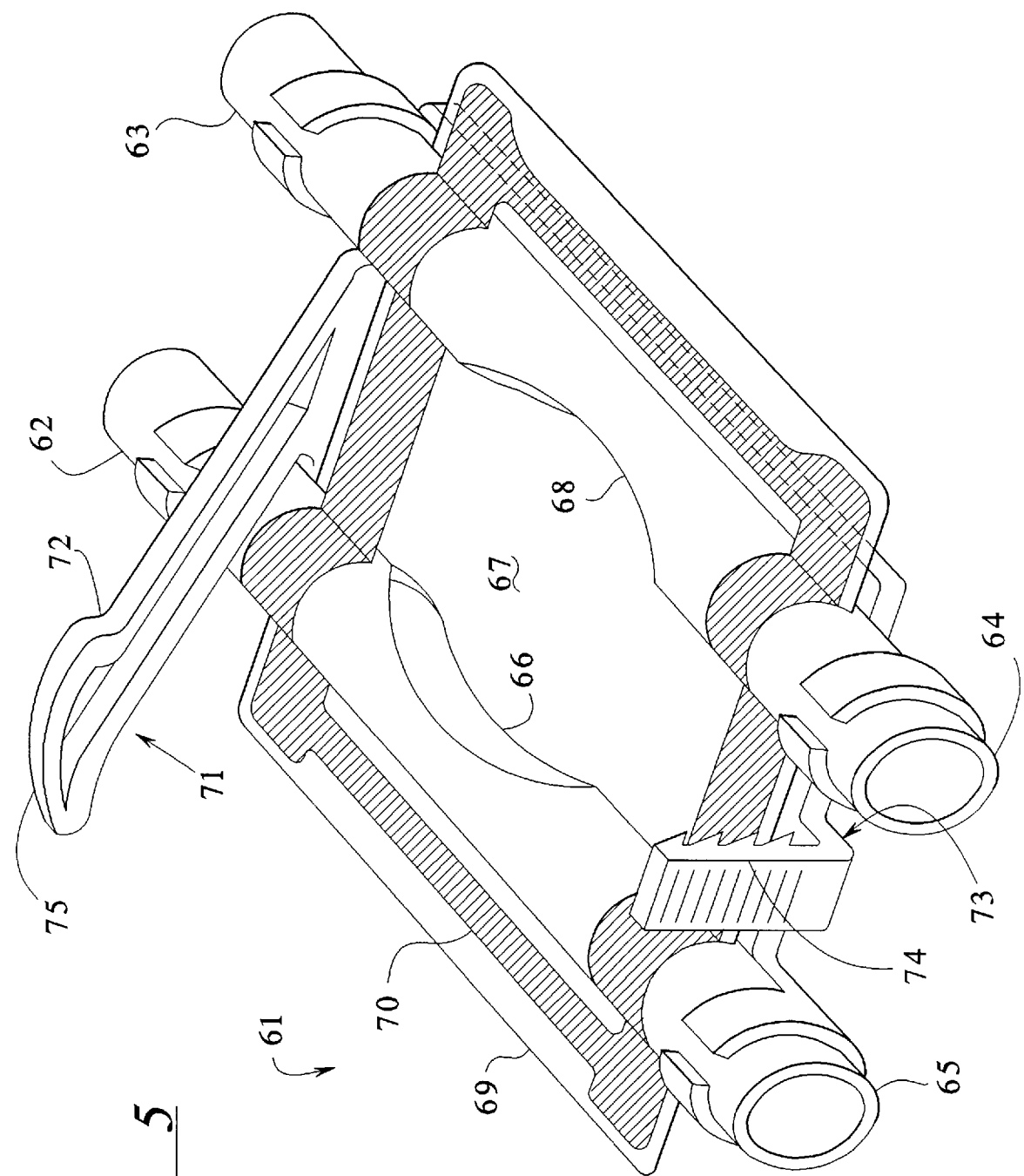
FIG. 5 illustrates a flexible fluid junction made in accordance with the present invention that links four fluid ducts and that further includes a clamp mechanism for isolating one pair of ducts from the other pair of ducts.

The present invention provides an improved flexible fluid junction that links three or more fluid ducts. As illustrated in FIG. 2, the flexible fluid junction 21 links tubes or fluid ducts 22, 23, 24. The tubes shown at 22, 23 and 24 may be bushings which are to be connected to longer tubes or fluid lines or the tubes 22, 23 and 24 may be connected directly to their respective fluid source or containers. Further, the tubes 23 and 24 are connected with an aperture 25 disposed therebetween. The tubes 22, 23 and 24 are disposed between two flexible webs including a lower web 26 and an upper web 27. The central portions of the webs 26, 27 have been cut away for clarity. The outer peripheries of the webs 26 and 27 are sealed together to form a chamber indicated generally at 28. The aperture 25 and end 29 of the tube 22 are disposed within the chamber 28. The chamber 28 serves as a mixing area for fluid flowing through the tubes 22, 23 and 24. Further, because the webs 26, 27 are flexible, the chamber 28 can be clamped or sealed off thereby isolating the tube 22 from the tubes 23, 24. An example of a suitable clamping mechanism is illustrated in FIG. 5. The outer peripheries of the webs 26, 27 are sealed, preferably, by a radio frequency (RF) process. Additionally, the outer peripheries can be sealed using heat, adhesives or other suitable processes.

The junction 21 illustrated in FIG. 2 would be especially suitable for the dialysis system shown in FIG. 1 although other uses are anticipated. Specifically, the solution line 16 could be connected to the tube 22 while the patient line 12 and drain line 13 could be connected to the tubes 23, 24 respectively. To isolate the solution line 16 and tube 22, a clamp could be placed across the chamber 28 between the tube 22 and the tubes 23, 24.

It will be noted that one of the tubes 22, 23, 24 may be eliminated to provide a two-tube junction. An example of such a junction is illustrated in FIG. 2A. Specifically, the junction 21a links two tubes 23a, 24a between a lower web 26a and upper web 27a. A chamber 28a is disposed between the webs 26a, 27a. The tubes 23a, 24a may also be connected like the tubes 23, 24 that are illustrated in FIG. 2.

Figure 3:
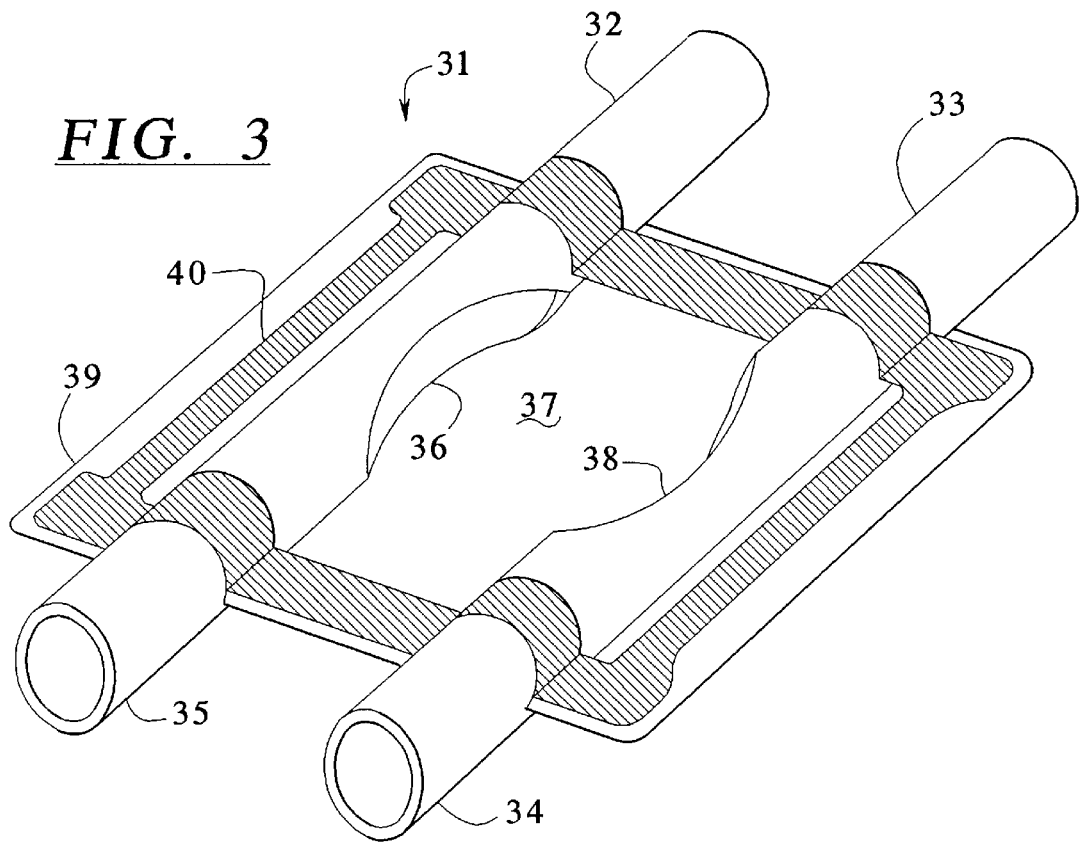
FIG. 3 illustrates a flexible fluid junction made in accordance with the present invention that links four fluid ducts.

FIG. 3 illustrates a flexible fluid junction 31 that links four tubes or fluid ducts 32, 33, 34, 35. In the embodiment illustrated in FIG. 3, the tubes 32, 35 are connected with an aperture 36 disposed between the tubes and within the chamber illustrated generally at 37. Similarly, the tubes 33, 34 are connected with an aperture 38 disposed between the tubes 33, 34 and within the chamber 37. The chamber is defined by the sealed outer peripheries of the lower web 39 and upper web 40. The webs 39, 40 are preferably sealed by an RF process or other suitable means as described above. The tubes 32, 35 and 33, 34 need not be connected as illustrated in FIG. 3; four separate tubes or bushings may be utilized.

Figure 4:
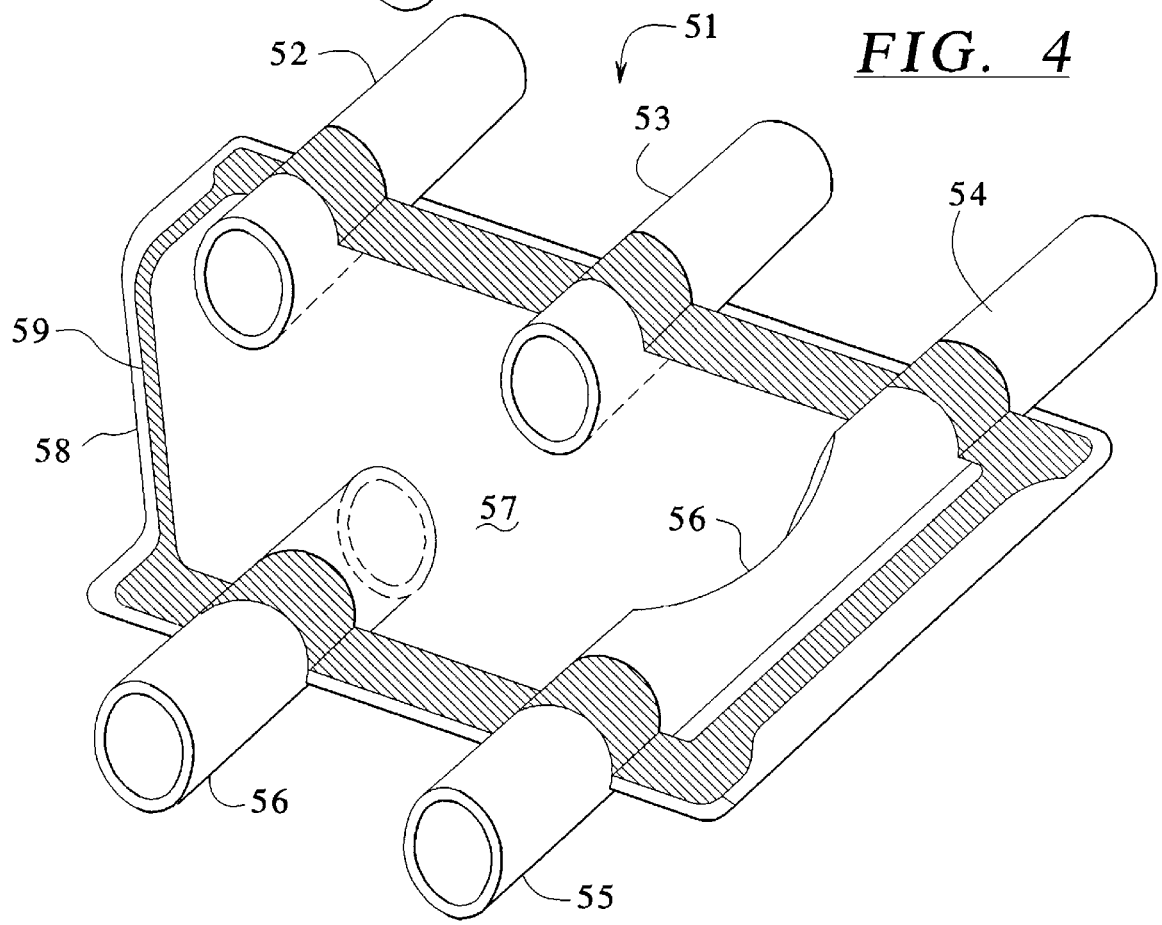
FIG. 4 illustrates a flexible fluid junction made in accordance with the present invention that links five fluid ducts.

As illustrated in FIG. 4, the present invention may also be utilized to construct a flexible fluid junction 51 that links five separate tubes or fluid ducts 52, 53, 54, 55, 56. Fluid junctions that link more than five fluid ducts are also possible. In the embodiment illustrated in FIG. 4, the tubes 54 and 55 are connected with an aperture 56 disposed therebetween and within the chamber shown at 57. The chamber is defined by the outer peripheries of the lower web 58 and upper web 59. Again, the outer peripheries of the webs 58, 59 may be joined by an RF process or other suitable means as discussed above.

FIG. 5 illustrates a flexible fluid junction 61 that links four tubes 62, 63, 64, 65. In the embodiment illustrated in FIG. 5, the tubes 62 and 65 are connected with the aperture 65 disposed therebetween and within the chamber 67. The tubes 63, 64 are also connected with an aperture 68 disposed therebetween and within the chamber 67. The chamber 67 is defined by the outer peripheries of the lower web 69 and upper web 70. Again, the peripheries of the webs 69, 70 are preferably sealed by an RF process or other suitable sealing means.

The junction 61 as illustrated in FIG. 5 also features a clamp mechanism 71 that includes an upper arm 72 that is pivotally connected to a lower arm 73. The distal end of the lower arm 73 features a latch 74 that engages the distal end 75 of the upper arm 72. The upper arm 72 pivots downward so that the end 75 engages the latch 74 to close or clamp the junction 61 thereby isolating the tubes 62, 65 from the tubes 63, 64. In effect, the clamp mechanism 71 presses the inside surfaces of the webs 69, 70 together to isolate the aperture 66 from the aperture 68. A clamp mechanism similar to that illustrated at 71 in FIG. 5 can also be utilized with three-duct junctions such as that illustrated at 21 in FIG. 2 and four-duct junctions such as that illustrated at 51 in FIG. 4.

The lower arm 73 of the clamp mechanism 71 is preferably attached to the lower web 69. By attaching the clamp mechanism 71 to the junction 61, the clamp mechanism 71 adds rigidity to the junction 61 which helps prevent the junction from being rolled or twisted which would thereby impede the flow of fluid through the junction 61 and specifically through the chamber 67. Additionally, if the material used to fabricate the tubes 62, 63, 64, 65 is a flexible material, any added rigidity provided by the clamp mechanism 71 will be beneficial.

The flexible webbings may be fabricated from a variety of materials. Preferably, the webbings are fabricated using an extrusion process due to its high speed and low cost. One preferred material for fabricating the webbing film is polyvinylchloride (PVC). Also, a film comprising a layer of PVC with a layer of copolyester such as PCCE may also be used. PCCE is a copolymer of polyether and polyethylene terephothalate and is sold by Eastman Chemical Co. The layer of PCCE is used to prevent sticking during the sterilization or autoclaving process. The PCCE layer also prevents bead formation during the RF sealing process. The prevention of the formation of beads on the web surfaces interferes with the ability of the clamp to seal off one side of the chamber from the other side of the chamber.

Additionally, the webs can be fabricated from commercially available films such as HYTREL containing ACRAWAX. HYTREL is available from DuPont Co. of Wilmington, Del. ACRAWAX is available from Lonza, Inc. of Fairlawn, N.J. The upper and lower webs need not be made from identical films. Specifically, one film can be made from HYTREL containing ACRAWAX and the second film can be fabricated from PCCE, PVC or PVC coated with PCCE. In addition to PVC coated with PCCE as discussed above, the films may comprise a layer of PCCE coated with PVC.

It is also anticipated that a temporary seal may be provided to separate one side of the chamber from the other side of the chamber which may be peelable. When ready, the seal may simply peeled apart to allow communication from one side of the chamber to the other.

All tubing and webbing components described above with respect to FIGS. 1 through 5 may be fabricated from extrusion processes. Also as discussed above, the tubes or ducts illustrated in FIGS. 1 through 5 may be bushings which are connected to longer tubes which are connected to containers or cavities or the tubes themselves may be sufficiently long enough to be connected to containers or cavities thereby eliminating the need for shorter bushings. The preferred material for fabricating the tubes or fluid ducts is PVC.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. A method of linking at least two containers, including a solution container, a drainage container, and at least one supply tube, without introducing air bubbles to the supply tube, the method comprising the following steps:

providing at least two containers including the solution container and the drainage container, providing a flexible fluid junction comprising a pair of flexible webs, each of the webs having an outer periphery, and at least three tubes including a solution tube, a drainage tube and a supply tube, each of said tubes being disposed between the flexible webs, the outer peripheries of the webs being sealed together and around the tubes to define a flexible mixing chamber, an end of each of the tubes terminating inside the chamber, isolating the solution tube from the drain and supply tubes with a clamp that extends across the flexible fluid junction between the solution tube and the drain and patient tubes, connecting the drain tube to the drain container, connecting the patient tube to a source of waste fluid, connecting the solution container to the solution tube, establishing fluid flow between the source of waste fluid and the drain container, removing the clamp.

2. The method of claim 1, wherein the solution tube and the drain tube are connected together with an aperture disposed between the tubes and between the flexible webs so that the aperture is disposed within the chamber.

3. A flexible fluid junction comprising:

a pair of flexible webs, each of the webs having an outer periphery, at least three tubes disposed between the flexible webs, the outer peripheries of the webs being sealed together and around the tubes to define a flexible mixing chamber, an end of each of the tubes terminating inside the chamber and, a clamp extending across exterior surfaces of the webs, the clamp, when in a closed position, presses interior surfaces of the webs together and isolates at least one of the tubes from the other tubes.

4. The flexible fluid junction of claim 3, wherein two of the tubes are connected together with an aperture disposed between the tubes and within the chamber.

5. The flexible fluid junction of claim 3, wherein the webs are formed by an extrusion process.

6. The flexible fluid junction of claim 3, wherein the clamp is connected to the exterior surface of one web and including an upper arm and a lower arm, the arms being pivotally connected together, the lower arm including a latch for engaging a distal end of the upper arm when the upper arm is pivoted downward toward the lower arm in a closed position, at least one of the tubes being isolated from the other tubes.

7. The flexible fluid junction of claim 3, wherein said junction is capable of being stored in the clamped position without substantial permanent deformation.

8. The flexible fluid junction of claim 3 further comprising a fourth tube, the fourth tube terminating inside the chamber and being sealably connected between the outer peripheries of the two webs.

9. The flexible fluid junction of claim 8, wherein the fourth tube is connected to one other tube with an aperture disposed between the tubes and within the chamber.

10. The flexible fluid junction of claim 8, further comprising a clamp extending across exterior surfaces of the webs, the clamp, when in a closed position, presses interior surfaces of the webs together and isolates two of the tubes from the other two tubes.

11. The flexible fluid junction of claim 3 further comprising a fourth tube and a fifth tube, the fourth and fifth tubes terminating inside the chamber and being sealably connected between the outer peripheries of the two webs.

12. The flexible fluid junction of claim 3, wherein the webs comprise a film selected from the group consisting of PVC, PVC coated with a copolyester, PVC laminated with a copolyester; PVC coextruded with a copolyester, a polyester block copolymer, a polyester block copolymer containing a lubricant, polyethylene, and polypropylene.

13. The flexible fluid junction of claim 3, wherein the outer peripheries of the webs being sealed together and to the tubes by RF.

14. A fluid exchange system comprising:

a patient tube, at least one solution line, at least one solution container, a drainage line, a drainage container, a flexible fluid junction comprising a pair of flexible webs, each of the webs having an outer periphery, and at least three tubes including a solution tube, a drainage tube and a supply tube, each of said tubes being disposed between the flexible webs, the outer peripheries of the webs being sealed together and around the tubes to define a flexible mixing chamber, an end of each of the tubes terminating inside the chamber, the solution tube being connected to the solution container, the drainage tube being connected to the drainage container and, a clamp extending across exterior surfaces of the webs, the clamp, when in a closed position, presses interior surfaces of the webs together and isolates at least one of the tubes and prevents flow from the isolated tube from entering the chamber.

15. The system of claim 14, wherein the solution tube and the drain tube are connected together with an aperture disposed between the tubes and between the flexible webs so that the aperture is disposed within the chamber.

\* \* \* \* \*